United States Patent [19]

Meneghini et al.

[11] Patent Number: 5,290,682

[45] Date of Patent: Mar. 1, 1994

[54] ENZYME CONTROLLED PROCESSES AND PRODUCTS

[75] Inventors: Frank A. Meneghini, San Carlos, Calif.; Paul S. Palumbo, West Newton, Mass.

[73] Assignee: Polaroid Corporation, Cambridge, Mass.

[21] Appl. No.: 708,472

[22] Filed: May 31, 1991

[51] Int. Cl.$^5$ .................... C12Q 1/26; G01N 33/566
[52] U.S. Cl. .................... 435/25; 435/117; 435/120; 435/125; 435/968; 436/501; 436/518; 436/536; 436/546; 436/172; 436/800; 436/805; 436/815; 436/904; 546/48; 549/227
[58] Field of Search ............. 435/25, 117, 120, 125, 435/968; 436/501, 518, 536, 546, 172, 800, 805, 815, 904; 536/27; 546/48

[56] References Cited

U.S. PATENT DOCUMENTS

| | | | |
|---|---|---|---|
| 2,983,606 | 5/1961 | Rogers | 106/21 |
| 4,536,219 | 8/1985 | Riou et al. | 106/21 |
| 4,900,686 | 2/1990 | Arnost et al. | 436/546 |
| 4,988,616 | 1/1991 | Heidenreich et al. | 436/904 |

FOREIGN PATENT DOCUMENTS

| | | | |
|---|---|---|---|
| 0098151 | 1/1984 | European Pat. Off. | B41M 5/26 |
| 0110682 | 6/1984 | European Pat. Off. | C12Q 1/28 |
| 58-97044 | 6/1983 | Japan | C09D 11/00 |

OTHER PUBLICATIONS

Van de Sande, C. C., Angew. Chem. Int. Ed., Eng. 22 (1983), pp. 191–209.
Neblette, Imaging Processes and Materials, 8th Ed., Van Nostrand Reinhold, N.Y., 1989, Ch. 9, pp. 290–291.
Carpenter, J. W., and Lauf, P. W., "Photothermographic Silver Halide Systems", Research Disclosure, No. 17029, Jun. 1978.

*Primary Examiner*—Michael G. Wityshyn
*Assistant Examiner*—Abdel A. Mohamed
*Attorney, Agent, or Firm*—Gaetano D. Maccarone

[57] ABSTRACT

Compounds which are useful as substrates for enzymes are disclosed. An enzyme-controlled process is provided for generating a colored species from an initially substantially colorless material as a result of enzymatic attack. The process can be exploited to provide an enzyme-amplified diagnostic assay method to detect an analyte of interest present in a test sample.

6 Claims, No Drawings

ENZYME CONTROLLED PROCESSES AND PRODUCTS

CROSS-REFERENCE TO RELATED APPLICATIONS

Reference is made to the commonly assigned copending application of Myron S. Simon, Marcis M. Kampe and David P. Waller Ser. No. 708,679, filed on even date herewith, and now U.S. Pat. No. 5,258,279.

BACKGROUND OF THE INVENTION

The present invention relates to enzyme controlled processes and products and, more particularly, to an enzyme controlled system for generating a fluorescent species as a result of enzyme oxidation of an oxidizable group.

Compounds and processes for detecting an analyte of interest in a sample fluid utilizing enzyme-labeled species are known in the art. The enzyme-labeled species can be made to interact with a substrate to cause a change in the color or fluorescence of the substrate and in this manner allow the enzyme label to be detected and to provide a quantitative determination of the analyte of interest. New substrate materials for use in such systems are of continuing interest.

It is therefore an object of this invention to provide an enzyme controlled system for generating a colored species from an initially substantially colorless material.

Another object is to provide a method for generating a colored species as a result of enzymatic oxidation of an oxidizable group.

Still another object is to provide a method for generating a colored species as a result of enzymatic oxidation of a hydroquinonyl group.

A further object is to provide an enzyme-amplified immunoassay system for detecting an analyte in a test sample.

SUMMARY OF THE INVENTION

These and other objects and advantages are accomplished in accordance with the invention by providing enzyme-controlled processes and products for generating a colored species from an initially substantially colorless material as a result of enzymatic attack. The processes and products of the invention utilize rhodamine compounds which have an oxidizable group and which are represented by the formula

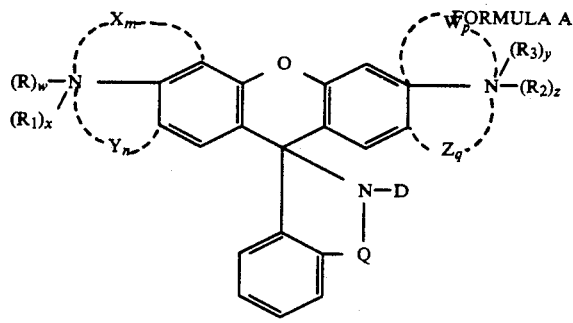

FORMULA A wherein W, X, Y and Z are the same or different and each is represented by $-(CH_2)_a-(CHR_4)- -(CH_2)_b-$;

D is a moiety which can be oxidized by an enzyme to a more electron deficient species, such as o- and p-hydroquinones, o- and p-aminophenols, anisidines, phenylenediamines, phenols and the like;

R, $R_1$, $R_2$, $R_3$ and $R_4$ each independently is hydrogen, alkyl, e.g., having from 1 to 6 carbon atoms, aryl such as phenyl or alkyl or aryl substituted with various substituents;

Q is $-CO$ or $-SO_2$;

a and b each independently is an integer of from 0 to 4, provided that the sum of a+b is an integer of from 1 to 4; and m, n, p, q, w, x, y and z each independently is 0 or 1, provided that the sum of m+n+w+x is 2 and the sum of p+q+y+z is 2.

As noted previously R, $R_1$, $R_2$, $R_3$ and $R_4$ each may be hydrogen, alkyl, aryl or substituted alkyl or aryl. These substituents may be used to immobilize the compound to a support such as a polymeric support. For example, one of these substituents may be a long chain ballast group such as an alkyl chain having 18 carbon atoms or more. The substituents may also include a hydrophilic or solubilizing, group, i.e., a group which will increase the solubility of the compound in water. Typical suitable solubilizing groups include carboxylic acids; polyethers such as polyethylene oxide; polyalcohols; primary, secondary or tertiary amines; polyamines; sulfonic acids; phosphoric acids or esters; phosphates and phosphate esters, etc.

The compounds within generic Formula A are substantially colorless. Because of the tetrahedral carbon of the central fused ring of the rhodamine moiety, the pi-interactions of the benzene rings on either side are insulated from each other. However, when the bond between this carbon atom and the nitrogen atom is heterolytically broken so as to make the carbon atom more electron deficient, the now trigonal carbon atom no longer insulates the pi-interactions of the fused benzene rings from each other. The pi-interactions of the benzene rings in the now conjugated system generate a color.

The break in the carbon-nitrogen bond which ultimately leads to the colored species is accomplished via enzymatic oxidation of the oxidizable group D. As noted previously, D can be any moiety which can be oxidized by an enzyme to a more electron deficient species. Preferred oxidizable groups are the o- and p-hydroquinonyl groups. Accordingly, for purposes of illustration, further discussion of the bondcleaving mechanism will be made with respect to the embodiment wherein D is a hydroquinonyl group. When attached to the hydroquinonyl group the nitrogen atom is relatively electron donating. However, when the hydroquinonyl group is oxidized to the quinone, the nitrogen atom becomes very much less electron donating, so much less so that the bond between the nitrogen atom is delocalized in the quinone ring. Accordingly, the enzyme which is utilized to oxidize the oxidizable group to the more electron deficient state should be one which can take part in redox reactions.

In some instances the chromophores resulting from the oxidation can be fluorophores. The fluorescent property can also be exploited in various applications.

The reaction by which the colored species is generated according to the invention is carried out in the presence of hydrogen peroxide. The hydrogen peroxide may be provided as one of the reaction materials or it may be generated in situ. For example, it is well known that the reaction of glucose oxidase with glucose and oxygen will provide gluconic acid and hydrogen peroxide.

Any suitable enzyme which will cause the oxidizable group to undergo oxidation to the more electron deficient state may be utilized. Typical suitable enzymes include phenoloxidases such as peroxidase, laccase, tyrosinase and the like.

DESCRIPTION OF THE PREFERRED EMBODIMENTS

Preferred compounds for use according to the invention are represented by the formulas:

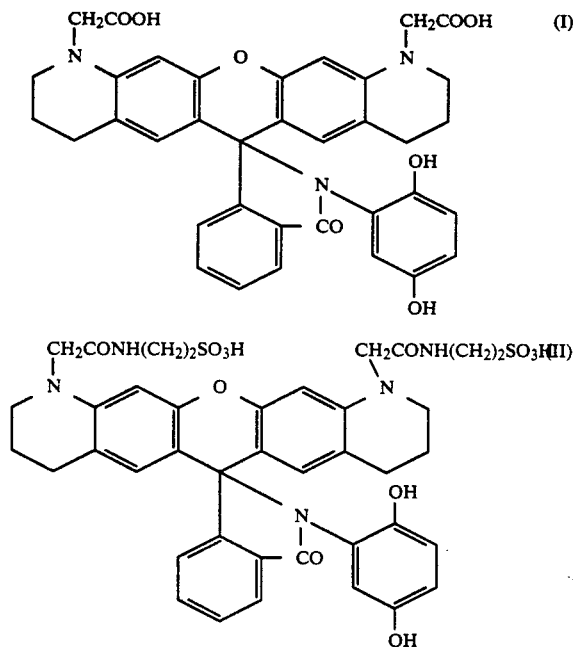

The compounds utilized according to the invention can be prepared by synthetic procedures which are known in the art and these will be apparent from the detailed preparative procedures which are described in the examples. Generally, the desired chromophoric moiety including any desired substituents is synthesized first. The substituents can be the blocked precursors to desired solubilizing or immobilizing groups. Synthetic techniques for preparing the desired chromophoric moieties are well known in the art. See, for example, U.S. Pat. No. 4,900,686. The oxidizable group, D, is then attached to the chromophoric moiety. Since the oxidizable group is attached to the chromophoric moiety through a nitrogen atom it is preferred to carry out this reaction step by coupling an amino group attached to the suitably protected oxidizable group to the carbonyl or sulfonyl group, Q. Any required further elaboration of the substituents can then be accomplished such as, for example, by removal of the protecting groups and formation of the desired substituents. The protecting groups present in the oxidizable group are then removed to reveal the desired oxidizable substrate. Suitably substituted and appropriately protected oxidizable groups can be prepared according to methods which are well known in the art.

The enzyme-controlled process for generating a colored species from a substantially colorless compound can be exploited for various applications. For example, the compounds may be used as substrates in enzyme-amplified immunoassay techniques. Such processes, which are well known in the art and therefore do not require extensive discussion here, include immunometric sandwich and competitive assays for an analyte e.g., an antigen or an antibody. In these assays an enzyme-labeled antigen or analyte is caused to take part in interactions with its binding partner to form a complex which is a function of the amount of analyte present in the test sample. Since the enzyme label must be detected indirectly a substrate is brought into contact with the complex to provide a colored species, which may also be fluorescent, and the now detectable species read out either visually or photometrically. The compounds may also be used in a determination for a particular enzyme in the test sample.

The invention will now be described further in detail with respect to specific preferred embodiments by way of examples it being understood that these are intended to be illustrative only and the invention is not limited to the materials, processes, etc., which are recited therein.

EXAMPLE I

To a stirred solution of a rhodamine dye (300 mg, 0.47 mmole) represented by the formula

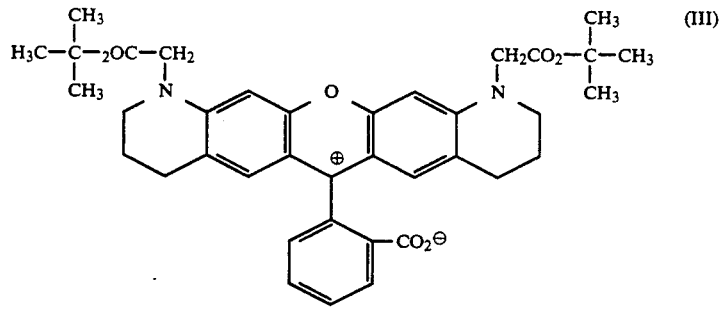

in 15 ml methylene chloride there was added 2-chloro-1-methylpyridinium iodide (240 mg, 0.94 mmole) in one portion and the resulting mixture stirred at room temperature under nitrogen for 10 minutes. To this solution there was added 2,5-dimethoxyaniline (144 mg, 0.94 mmole) and triethylamine (130 μl, 0.94 mmole) and stirring was then continued overnight at room temperature. The solvents were removed on a rotary evaporator and the resulting residue chromatographed on silica. The non-polar fraction, which eluted as a colorless spot on TLC and which turned purple upon exposure to acid, was collected and dried to yield 350 mg (96% yield) of a compound represented by the formula

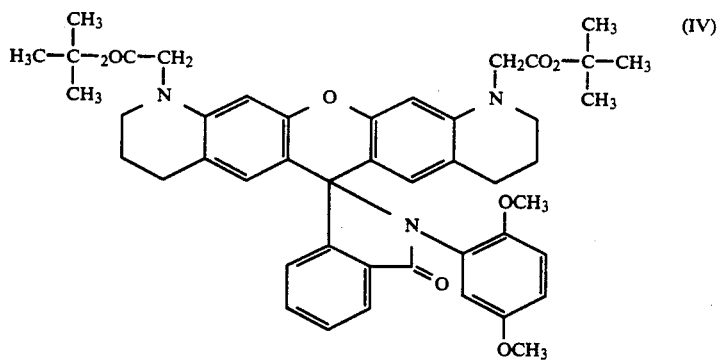

¹HNMR (CDCl₃) δ8.0-8.05 (m, 1H), 7.5-7.55 (m, 2H), 7.15-7.2 (m, 1H), 6.62 (s, 2H), 6.4 (s, 2H), 5.95 (s, 2H), 5.8 (s, 1H), 3.8 (bs, 4H), 3.4 (s, 3H), 3.35 (s, 3H), 3.3-3.4 (m, 4H), 2.5-2.6 (m, 4H), 1.8-1.95 (m, 4H), 1.45 (s, 18H). ¹³C NMR (CDCl₃) δ169.62 (s), 166.53(s), 152.58(s), 151.76(s), 150.02(s), 145.58(s), 132.39(d), 132.03(s), 128.68(d), 128.07(d), 124.62(s), 124.35(d), 123.36(d), 118.20(s), 115.75(d), 112.97(d), 112.52(d), 107.10(s), 96.56(d), 81.71(s), 67.74(s), 55.92(q), 55.47(q), 53.90(t), 50.44(t), 28.23(q), 27.51(t), 22.48(t).

A solution of compound (IV) (550 mg, 0.71 mmole) in 10 ml of methylene chloride was treated with 10 ml of trifluoroacetic acid and the resultant mixture stirred at room temperature under nitrogen for three hours. The volatile components were removed on a rotary evaporator to provide 530 mg (96% yield) of a purple solid represented by the formula

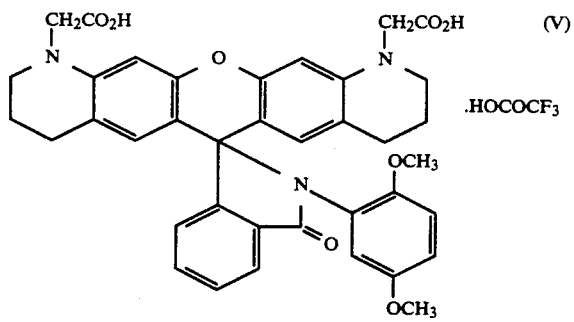

Thin layer chromatography of this material on reverse phase silica gel using 40% H₂O in MeOH as the eluent gave a colorless, ultraviolet spot (Rf≈0.75) which colorized with exposure to acid fumes.

¹H NMR (CDCl₃) δ8.3-6.3 (complex multiplet, 12H), 4.4-4.0 (b, 4H), 3.5 (bs, 6H), 2.9-2.5 (b, 4H), 2.1-1.6 (b, 4H), M.S. (FAB+): 662.

EXAMPLE II

A solution of compound V (108 mg, 0.163 mmole) is 5 ml of 1,2-dichloroethane was treated with a solution of boron tribromidedimethyl sulfide (500 mg, 1.60 mmole) in 4 ml of 1,2-dichloroethane and the resulting mixture refluxed for 4 hours. After standing at room temperature overnight the solution was treated with water, stirred vigorously and the resultant layers separated. The aqueous phase was made acidic by adding conc. HCl and precipitation of the product induced by introducing sodium chloride. The product was chromatographed on reverse phase silica gel using 40% H₂O in CH₃OH as the eluent to give 10 mg of compound I as the highest Rf material. An additional 10 mg was obtained via evaporation of the organic phase followed by the same recovery procedure. The compound was unstable in air and basic water.

¹HNMR (d7-DMF) δ7.8-7.9 (m, 1H), 7.5-7.65 (m, 2H), 7.0-7.1 (m, 1H), 6.7-6.5 (m, 4H), 6.55 (s, 2H), 6.15 (s, 2H), 6.0 (s, 1H), 5.8 (s, 2H), 4.1 (AB QUARTET, 4H), 3.2-3.4 (m, 4H), 2.4-2.65 (m, 4H), 1.65-1.9 (m, 4H); M.S. (FB+) 634; $\lambda_{max}^{pH7}$ 569 nm ($\epsilon$=2880).

EXAMPLE III

A mixture of compound V (10 mg, 0.015 mmole), taurine (6 mg, 0.045 mmole) and triethylamine (21 μl, 0.15 mmole) in 2 ml of dry dimethylformamide was treated in one portion with diphenylphosphorylazide (13 μl, 0.060 mmole) at −30° C. The resultant mixture was allowed to slowly warm to room temperature under nitrogen and then stirred for 6 hours. The volatile components were removed with a vacuum pump and the resulting residue chromatographed on reverse phase silica gel with 40% H₂O in MeOH as the eluent to give 10 mg (76% yield) upon trituration/filtration with Et₂O/CH₃CN of a compound represented by the formula

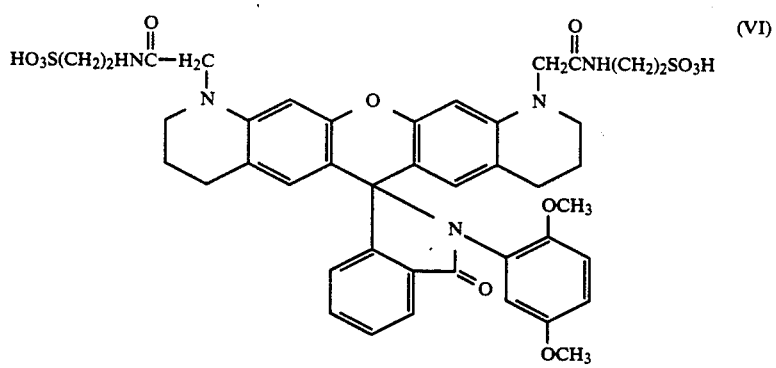

M.S. (FAB+): 876; λ max (pH 7.0 phosphate buffer) 490 nm (ε=240); 524 nm (ε=270).

EXAMPLE IV

A solution of compound VI (180 mg. 0.20 mmole) in 6 ml of 1,2-dichloroethane was treated with boron tribromide-dimethyl sulfide (650 mg, 2.08 mmole) and the resultant mixture refluxed under nitrogen for 6 hours and allowed to stand at room temperature overnight. The reaction mixture was diluted with methylene chloride, transferred to a separatory funnel and extracted with water. The aqueous phase was evaporated to dryness, evaporated twice from EtOH-HCl solution and then chromatographed on reverse phase silica gel with 50% $H_2O$ in $CH_3OH$ as the eluent to give 110 mg (65% yield) of compound II.

TLC of the product on silica gel with 50% $H_2O$ in $CH_3OH$ as the eluent showed a colorless, ultraviolet active spot (Rf 0.5) which turned pink upon exposure to NaOH-air.

$^1$H NMR (CD$_3$OD) δ8.0–8.1 (m, 1H) 7.8–7.85 (m, 2H), 7.45–7.5 (m, 1H), 7.35–7.4 (m, 2H), 7.2–7.25 (m, 3H), 7.05–7.1 (bs, 3H), 6.7 (s, 2H), 6.6 (d, J=7.5 HZ, 1H), 6.36 (dd, J$_1$=7.5 HZ, J$_2$=3 HZ, 1H), 4.3 (bs, 4H), 3.68 (t, J=5 HZ, 4H), 3.55–3.65 (m, 4H), 3.02 (t, J=5 HZ, 4H), 2.74–2.85 (m, 4H), 1.95–2.10 (m, 4H); M.S. (FAB+) 849; ε$_{max}^{pH7}$ 554 nm (ε=1360).

EXAMPLE V

Compound II was incorporated into solutions of pH 4.5, 5.5 and 6.0, respectively, by combining 1 ml of a 1 mmolar solution of the compound with varying amounts of 0.02 molar citrate buffer with 5% gelatin.

Assay solutions were made from these by combining 1 ml of the substrate solution, 3 μl (0.9M.) $H_2O_2$, and 10 μl (10 μg/ml) of a horseradish peroxidase solution. In addition, assay solutions were also prepared by adding to the above described solutions either 100 μl of 2.0 mmolar p-iodophenol or hydroquinone.

These assay solutions were incubated for 10 minutes in a spectrophotometer. Subsequently 100 μl of the assay solution were removed, diluted with 900 μl of pH 6 citrate buffer and scanned immediately using a pH 6 buffer as the reference sample. The optical density (OD) of the solutions after 1 minute is shown in Table I. The OD results shown represent the optical density units above background/min: (optical density in the presence of all the reagents except the enzyme).

| pH | Additives | OD/min. |
| --- | --- | --- |
| 4.5 | $H_2O_2$ | 0.148 |
| 4.5 | $H_2O_2$ p-iodophenol | 0.649 |
| 4.5 | $H_2O_2$ hydroquinone | 1.273 |
| 5.5 | $H_2O_2$ | 0.109 |
| 5.5 | $H_2O_2$ p-iodophenol | 1.124 |
| 5.5 | $H_2O_2$ hydroquinone | 0.644 |
| 6.0 | $H_2O_2$ | 0.159 |
| 6.0 | $H_2O_2$ p-iodophenol | 2.035 |
| 6.0 | $H_2O_2$ hydroquinone | 0.758 |

It can be seen that the horseradish peroxidase was effective to convert the initially substantially colorless compound II to a colored state under the experimental conditions.

Although the invention has been described with respect to specific preferred embodiments it is not intended to be limited thereto but rather those skilled in the art will recognize that variations and modifications may be made therein which are within the spirit of the invention and the scope of the appended claims. For example, it has been described that the compounds within Formula A can be immobilized to a solid support through any of substituents R, R$_1$, R$_2$, and R$_3$ or these substituents can also include a hydrophilic, or solubilizing group. Those skilled in the art will appreciate that the other cyclic ring in the compounds represented by Formula A or a cyclic ring present in the oxidizable group, D, such as the hydroquinonyl group, could be substituted in the same way for the purposes of immobilizing the molecule or improving its solubility. Thus, analogs processing the advantageous features of the compounds used according to the invention will be considered as equivalents thereof for the purposes of the claims herein.

What is claimed is:

1. A process for converting an initially substantially colorless compound to a colored species comprising reacting a substantially colorless compound represented by the formula

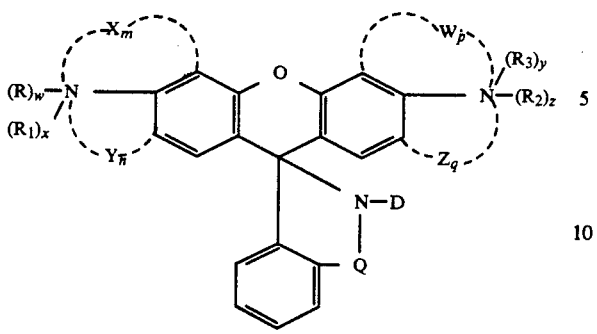

wherein W, X, Y and Z are the same or different and each is represented by $-(CH_2)_a-(CHR_4)--(CH_2)_b$;

D is a moiety which can be oxidized by an enzyme to a more electron deficient species; R, $R_1$, $R_2$, $R_3$, $R_4$ each independently is hydrogen, alkyl or aryl;

Q is —CO or —$SO_2$;

a and b each independently is an integer of from 0 to 4, provided that the sum of a+b is an integer of from 1 to 4; and m, n, p, q, w, x, y and z each independently is 0 or 1, provided that the sum of m+n+w+x is 2 and the sum of p+q+y+z is 2;

with an enzyme or an enzyme labeled antigen or antibody in the presence of hydrogen peroxide to form a colored species, wherein said enzyme or said enzyme labeled antigen or antibody oxidizes said oxidizable moiety D to a more electron deficient species.

2. The process as defined in claim 1 wherein said oxidizable moiety D is selected from the group consisting of o- and p-hydroquinones, o- and p-aminophenols, anisidines, phenylenediamines and phenols.

3. The process as defined in claim 1 wherein said hydrogen peroxide is generated in situ.

4. The process as defined in claim 1 and further comprising the step of detecting said colored species.

5. The process as defined in claim 4 wherein an enzyme-labeled antigen or antibody is reacted with said substantially colorless compound.

6. The process as defined in claim 1 wherein said enzyme or said enzyme labeled antigen or antibody is a phenoloxidase.

* * * * *